United States Patent [19]

Rempfler

[11] Patent Number: 4,999,046
[45] Date of Patent: Mar. 12, 1991

[54] N-(2-NITROPHENYL)-N-PYRIMIDIN-2-YLUREAS

[75] Inventor: Hermann Rempfler, Ettingen, Switzerland

[73] Assignee: Ciba-Geigy Corporation, Ardsley, N.Y.

[21] Appl. No.: 333,377

[22] Filed: Apr. 5, 1989

[30] Foreign Application Priority Data

Apr. 12, 1988 [CH] Switzerland .................. 1335/88

[51] Int. Cl.$^5$ .................... A01N 43/54; C07D 239/42
[52] U.S. Cl. ......................................... 71/92; 544/332
[58] Field of Search ............................. 544/332; 71/92

[56] References Cited

U.S. PATENT DOCUMENTS 4,659,363  4/1987  Hubele et al. ............................ 71/92
4,694,009  9/1987  Hubele et al. ......................... 514/269
4,783,459 11/1988  Buhmann et al. ................. 514/235.8
4,802,909  2/1989  Rempfler et al. ....................... 71/92

FOREIGN PATENT DOCUMENTS 151404 10/1981 German Democratic Rep. .

OTHER PUBLICATIONS

Rempfler, et al., "Chemical Abstracts," vol. 109, 1988, Col. 109; 33864g.

Primary Examiner—Glennon H. Hollrah
Assistant Examiner—James H. Turnipseed
Attorney, Agent, or Firm—Kevin T. Mansfield; Edward McC.Roberts

[57] ABSTRACT

The present invention relates to novel N-(2-nitrophenyl)-N-pyrimidin-2-ylureas having a herbicidal and plant growth-regulating activity, to agrochemical compositions containing those substances as active ingredients, to the use of the novel ureas for controlling weeds or for regulating plant growth, and to processes for the preparation of the novel compounds. The invention also relates to novel intermediates and to processes for the preparation thereof.

The novel compounds correspond to formula I

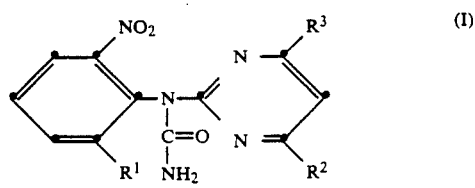

in which
$R^1$ is hydrogen, methyl, fluorine, chlorine or bromine,
$R^2$ is $C_1$–$C_2$haloalkyl having at least 2 fluorine atoms, and
$R^3$ is $C_1$–$C_4$alkyl,
with the proviso that $R^2$ is not trifluoromethyl when $R^3$ is methyl.

11 Claims, No Drawings

N-(2-NITROPHENYL)-N-PYRIMIDIN-2-YLUREAS

The present invention relates to novel N-(2-nitrophenyl)-N-pyrimidin-2-ylureas having a herbicidal and plant growth-regulating activity, to agrochemical compositions containing those substances as active ingredients, to the use of the novel ureas for controlling weeds or for regulating plant growth, and to processes for the preparation of the novel compounds. The invention also relates to novel intermediates and to processes for the preparation thereof.

(Pyrimidin-2-yl)-2-nitroanilines are known from Patent Specification DD-151 404 and from European Patent Application EP-A-No. 0 172 786. These compounds are fungicidally active. In contrast, it has surprisingly been found that N-pyrimidin-2-yl-N-2-nitrophenylureas have a herbicidal and plant growth-regulating activity.

The invention relates to ureas of formula I

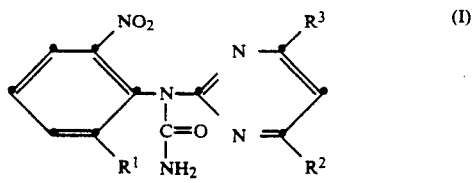

in which
$R^1$ is hydrogen, methyl, fluorine, chlorine or bromine,
$R^2$ is $C_1$-$C_2$haloalkyl having at least 2 fluorine atoms, and
$R^3$ is $C_1$-$C_4$alkyl, with the proviso that $R^2$ is not trifluoromethyl when $R^3$ is methyl, and to the salts and addition compounds of the ureas of formula I with acids, bases or complex formers.

Within the scope of the invention disclosed herein, the generic terms used include, for example, the following specific individual substituents, without this list implying any limitation of the invention:

$C_1$-$C_4$alkyl is methyl, ethyl, n-propyl, isopropyl, n-butyl, sec.-butyl, isobutyl or tert.-butyl, with methyl, ethyl, n-propyl, isopropyl, sec.-butyl and isobutyl being preferred.

Haloalkyl radicals are especially difluorochloromethyl, difluoromethyl, trifluoromethyl, 1,1-difluoro-2,2,2-trichloromethyl, 1,1-dichloro-2,2,2-trifluoromethyl, pentafluoroethyl, 1,1,2,2-tetrafluoro-2-chloroethyl, 1,1,2,2-tetrafluoroethyl, 1,1,2-trifluoroethyl, 1,2,2,2-tetrafluoroethyl and 1,2,2-trifluoroethyl.

Preferred are compounds of formula I in which
$R^1$ is hydrogen, methyl, fluorine, chlorine or bromine,
$R^2$ is chlorodifluoromethyl, difluoromethyl, 1,1-difluoro-2,2,2-trichloroethyl, 1,1-dichloro-2,2,2-trifluoroethyl, pentafluoroethyl, 1,1,2,2-tetrafluoro-2-chloroethyl or trifluoromethyl and
$R^3$ is $C_1$-$C_4$alkyl.

Especially preferred are compounds of formula I in which
$R^1$ is hydrogen, methyl, fluorine, chlorine or bromine,
$R^2$ is chlorodifluoromethyl, difluoromethyl, 1,1-difluoro-2,2,2-trichloroethyl, 1,1-dichloro-2,2,2-trifluoroethyl, pentafluoroethyl, 1,1,2,2-tetrafluoro-2-chloroethyl or trifluoromethyl and
$R^3$ is methyl, ethyl, n-propyl, isopropyl, sec.-butyl or isobutyl.

Attention is drawn to compounds of formula I in which
$R^1$ is hydrogen or methyl,
$R^2$ is trifluoromethyl and
$R^3$ is methyl, ethyl or isopropyl.

The following individual compounds may be mentioned: 2-[N-carbamoyl-N-(6-methyl-2-nitrophenyl)-amino]-4-trifluoromethyl-6-ethyl-pyrimidine and 2-[N-carbamoyl-N-(2-nitrophenyl)-amino]-4-trifluoromethyl-6-ethyl-pyrimidine.

The compounds of formula I can be prepared by
(a) reacting an aniline of formula II with phosgene to form a carbamoyl chloride of formula III and reacting this with $NH_3$ in a second step

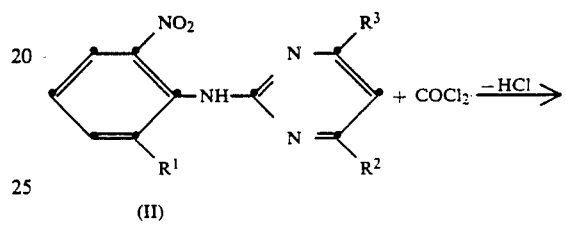

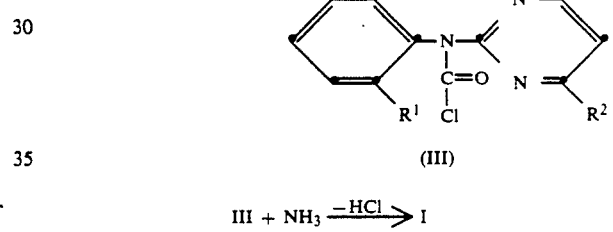

$$III + NH_3 \xrightarrow{-HCl} I$$

to form a urea of formula I, or
(b) reacting an aniline of formula II with a halosulfonyl isocyanate to form a halosulfonylurea of formula IV

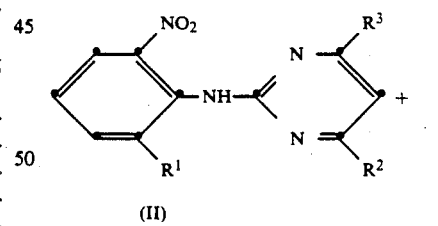

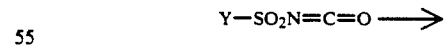

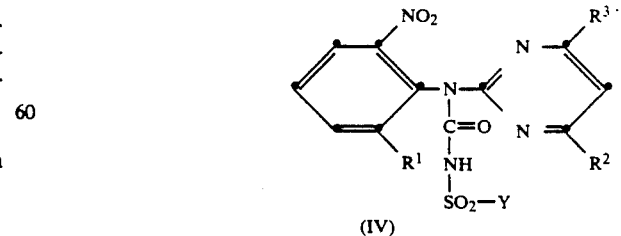

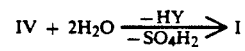

and hydrolysing this in a second step, or directly, to a compound of formula I, Y being a group that can be removed under the reaction conditions, such as halogen, preferably chlorine, or (c) rearranging a sulfonylurea of formula v, under the action of an aqueous base, to form a urea of formula I

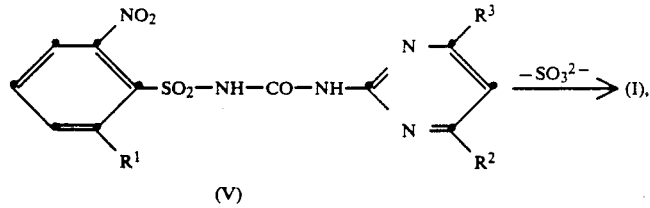

NaOH/water or KOH/water preferably being used as aqueous bases.

The reactions II→III, III→I and IV→I, which proceed with the removal of hydrogen halide or the elimination of HY, are preferably carried out using acid-binding agents (bases).

Suitable acid-binding agents are organic or inorganic bases, for example tertiary amines, such as trialkylamines (trimethylamine, triethylamine, tripropylamine etc.), pyridines (pyridine, 4-dimethylaminopyridine, 4-pyrrolidylaminopyridine etc.), and alcoholates, such as, for example, potassium tert.-butoxide, sodium methoxide or sodium ethoxide. The aforementioned reactions, including also the reaction V→I, can also be carried out with bases under phase transfer conditions according to processes that are known per se. (Lit. Dehmlow & Dehmlow, Phase Transfer Catalysis Verlag Chemie, Weinheim, 1983).

It is possible, in principle, for one or more solvents or diluents that are inert towards the reaction to be present in process variants (a) and (b), should there be no specific details given. Suitable solvents or diluents are, for example, aliphatic and aromatic hydrocarbons, such as benzene, toluene, xylenes, petroleum ether; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert.-butylmethyl ether etc.), anisole, dioxan, tetrahydrofuran; nitriles, such as acetonitrile, propionitrile; N,N-dialkylated amides, such as dimethylformamide; dimethyl sulfoxide; ketones, such as acetone, diethyl ketone, methyl ethyl ketone; and mixtures of such solvents with each other.

The 2-nitroanilines of formula II, like the novel carbamoyl chlorides of formula III and the novel ureas of formula IV, are valuable intermediates for the synthesis of herbicidally active ureas I.

The invention accordingly relates also to the novel compounds of formula II

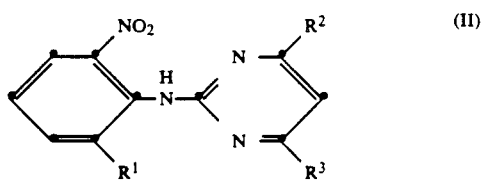

in which
$R^1$ is hydrogen, methyl, fluorine, chlorine or bromine,
$R^2$ is $C_1$–$C_2$haloalkyl having at least 2 fluorine atoms, and
$R^3$ is $C_1$–$C_4$alkyl,
with the proviso that $R^2$ is not trifluoromethyl when $R^3$ is methyl.

Furthermore, the invention relates to novel carbamoyl chlorides of formula III

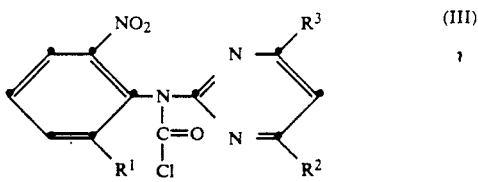

in which
$R^1$ is hydrogen, methyl, fluorine, chlorine or bromine,
$R^2$ is $C_1$–$C_2$haloalkyl having at least 2 fluorine atoms, and
$R^3$ is $C_1$–$C_4$alkyl,
with the proviso that $R^2$ is not trifluoromethyl when $R^3$ is methyl, and to ureas of formula IV

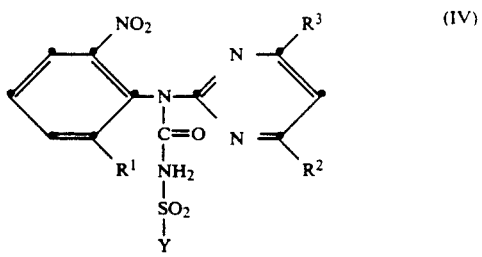

in which
Y is halogen,
$R^1$ is hydrogen, methyl, fluorine, chlorine or bromine,
$R^2$ is $C_1$–$C_2$haloalkyl having at least 2 fluorine atoms, and
$R^3$ is $C_1$–$C_4$alkyl,
with the proviso that $R^2$ is not trifluoromethyl when $R^3$ is methyl.

The compounds of formulae III and IV are intermediates of processes (a) and (b) and can be prepared, as described, from the corresponding 2-nitroanilines of formula II.

The novel 2-nitroanilines of formula II can be prepared analogously to processes known from the literature, for example by (d) reacting a guanidine of formula VI with a 1,3-dicarbonyl compound of formula VII

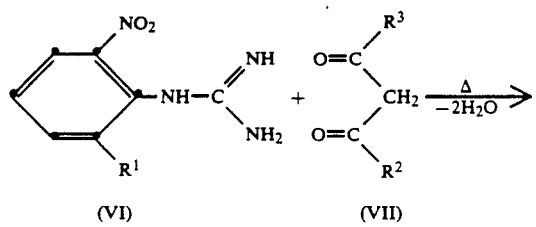 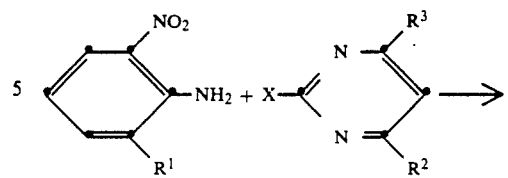

(VI)  (VII)  (XIV)  (XII)

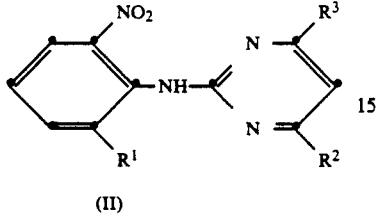 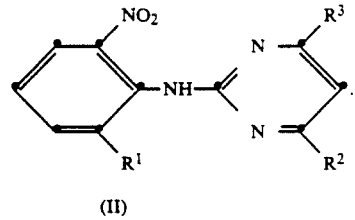

(II)  (II)

the condensation reaction if desired being carried out in the presence of a water-binding agent (Lit.: D. J. Brown in "The Chemistry of Heterocyclic Compounds" Vol. VI 1962, Interscience Publ. New York), or (e) reacting a halobenzene of formula VIII with a 2-aminopyrimidine of formula IX The sulfonylureas V are obtainable analogously to processes known from the literature by (h) reacting a sulfonamide X, in which $R^1$ is as defined hereinbefore, with phosgene to form an isocyanate XI, and then allowing this to react with a 2-aminopyrimidine IX to form V:

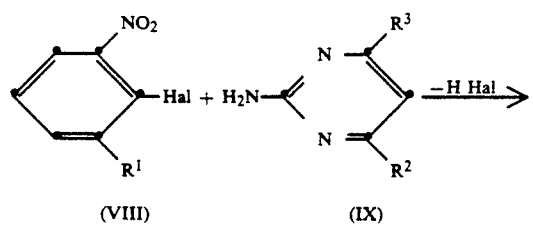 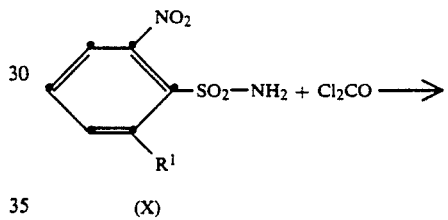

(VIII)  (IX)  (X)

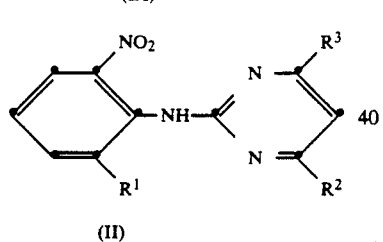 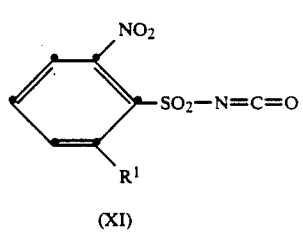

(II)  (XI)

analogously to EP-A-0 172 786, or (f) decomposing a sulfonylurea of formula V under the action of an aqueous base

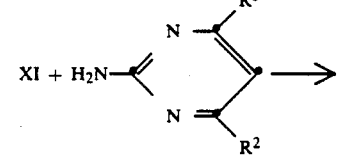

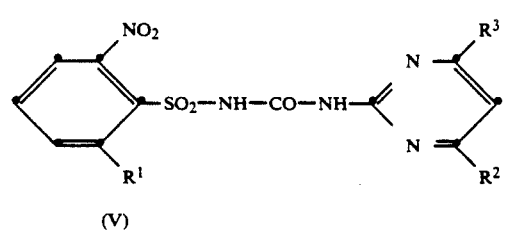 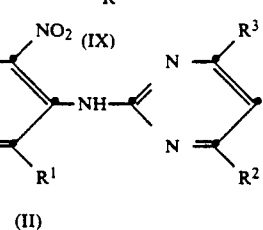

(V)  (II)

at elevated temperature, or (g) reacting an aniline of formula XIV with a pyrimidine of formula XII, in which formulae the radicals $R^2$ and $R^3$ are as defined hereinbefore an X is a nucleofugal group, such as halogen, $C_1$-$C_4$alkylsulfonyl or phenylsulfonyl

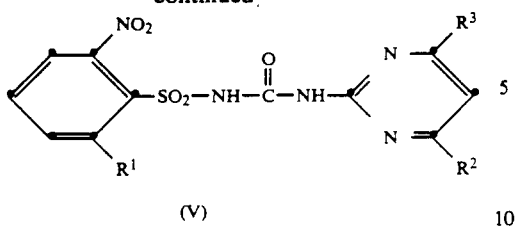

(V)

or (i) reacting a 2-aminopyrimidine IX, in which $R^2$ and $R^3$ are as defined hereinbefore, with phosgene to form an isocyanate XIII, and then allowing this to react with a sulfonamide X, in which $R^1$ is as defined hereinbefore, to form V:

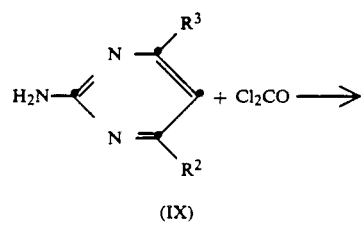

(IX)

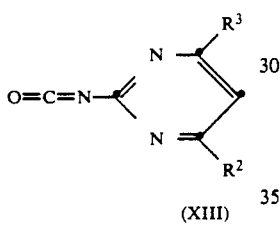

(XIII)

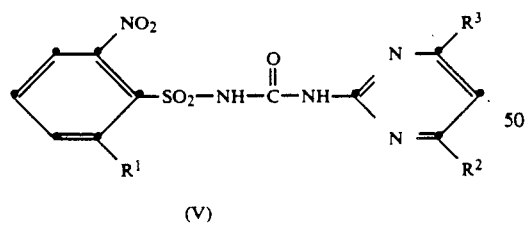

(X)

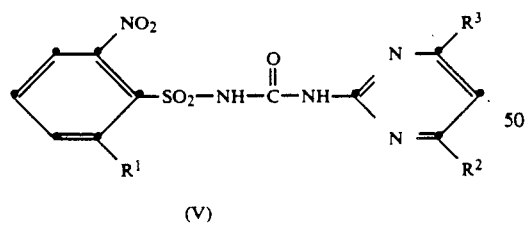

(V)

The guanidines VI can be prepared analogously to processes known from the literature by (j) reacting an aniline XIV, in which $R^1$ is as defined hereinbefore, with cyanamide:

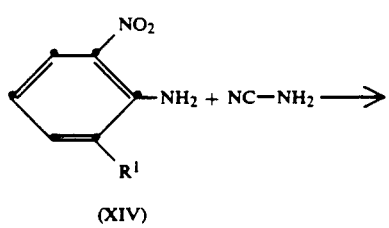

(XIV)

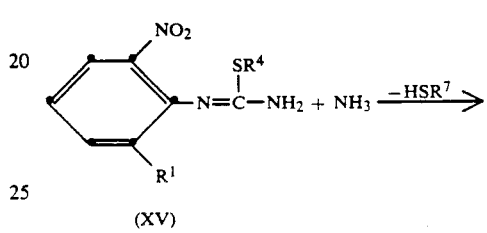

(VI)

or (k) reacting a thiourea ($R^4$=H) or an isothiourea ($R^4$=$C_1$-$C_4$alkyl) of formula XV, in which $R^1$ is as defined hereinbefore and $R^4$ is hydrogen or $C_1$-$C_4$alkyl, with ammonia to form the guanidine VI:

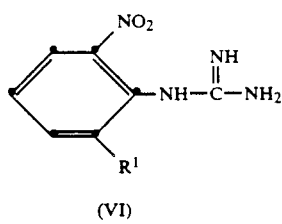

(XV)

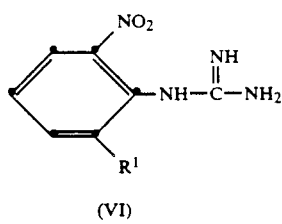

(VI)

(Literature: process j): Houben-Weyl, Methoden der Org. Chemie, Thieme, Stuttgart, Vol. VIII p. 98, 180; process k): Houben-Weyl, Methoden der Org. Chemie, Thieme, Stuttgart, Vol. VIII p. 183).

The β-diketones VII can also be prepared analogously to processes known from the literature by (l) reacting, under the reaction conditions of a Claisen condensation, a ketone XVI, in which $R^2$ is as defined hereinbefore, with a compound of formula XVII, in which $R^3$ is as defined hereinbefore and Z is a group that can be removed under the reaction conditions of a Claisen condensation, such as $C_1$-$C_4$alkoxy, phenoxy, benzyloxy or halogen,

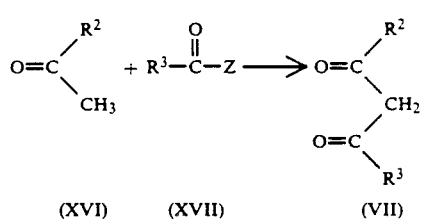

(XVI)   (XVII)   (VII)

or (m) reacting, under the reaction conditions of a Claisen condensation, a ketone XIX, in which $R^3$ is as defined hereinbefore, with a compound of formula XVIII, in which $R^2$ is as defined hereinbefore and Z is a group that can be removed under the reaction conditions of a Claisen condensation, such as $C_1$-$C_4$alkoxy, phenoxy, benzyloxy or halogen,

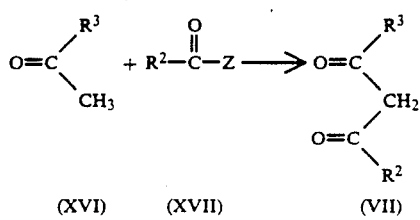

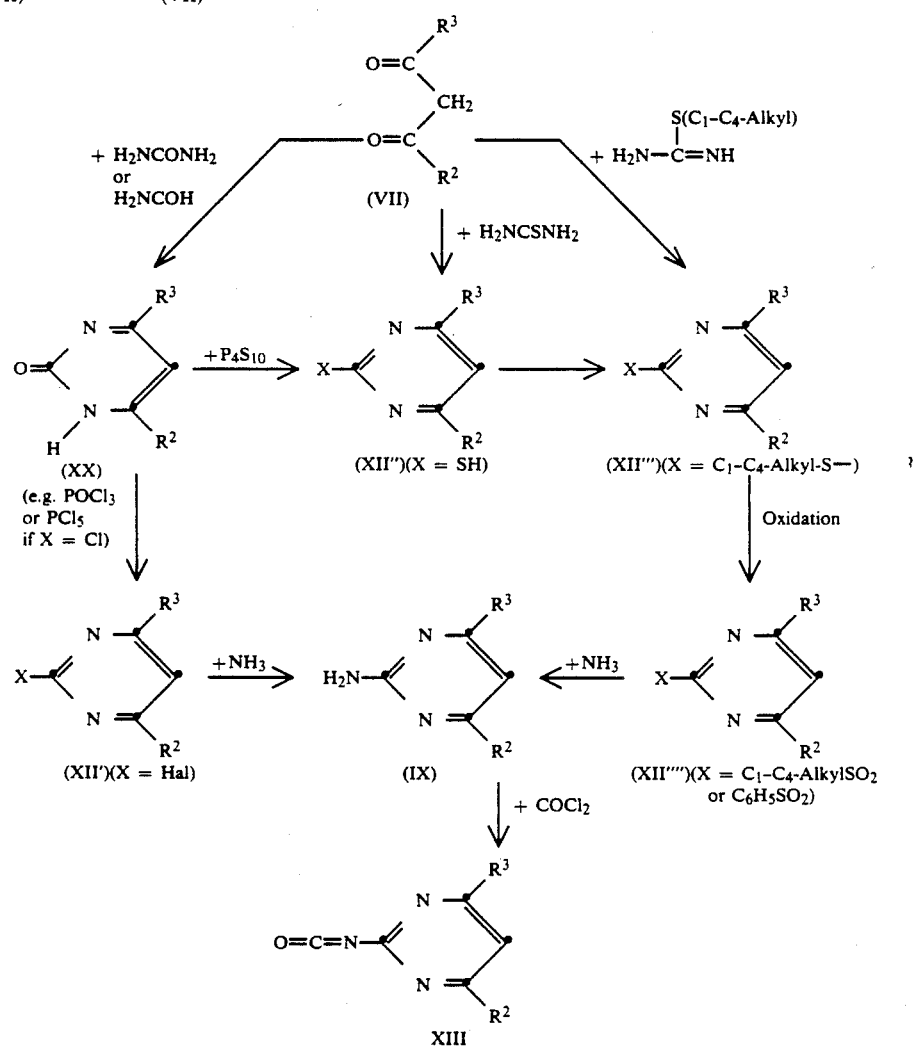

The following synthesis scheme (Scheme I) shows an extract of the possible methods of preparing these compounds, the β-diketone VII being used as starting material in each case:

Scheme I (Lit.: C. Ferry Reaktionen der organischen Synthese, Thieme Stuttgart, 1978 p. 312 and the literature cited therein).

The 2-aminopyrimidines IX, the 2-isocyanopyrimidines XIII, the 2-halopyrimidines XII' (in which X=halogen), the 2-mercaptopyrimidines XII'' (in which X=SH), the 2-alkylsulfonyl- or 2-phenylsulfonyl-pyrimidines XII'''' and the 2-alkylthiopyrimidines XII''' (in which X=$C_1$-$C_4$alkylthio or phenylthio), in which compounds the radicals $R^2$ and $R^3$ are as defined hereinbefore, are in most cases novel.

There are numerous methods of synthesis to the skilled person for the preparation of the compounds of formulae XIII, XII', XII'' and XII'''. These are gener- ally known to the chemist and are described comprehensively in the relevant textbooks.

The pyridinones XX, in which the radicals $R^2$ and $R^3$ are as defined hereinbefore, are also novel.

The invention furthermore relates to herbicidal and plant growth-regulating compositions containing a compound of formula I together with suitable adjuvants and/or carriers.

The active ingredients of the formula I are in general used successfully at application rates of from 0.005 to 5 kg/ha, especially from 0.1 to 3 kg/ha. The dosage necessary to achieve the desired effect can be ascertained by tests. It is dependent upon the nature of the action, the stage of development of the crop plant and of the weed and on the application (locus, time, method), and may vary within wide ranges, subject to these parameters.

At lower rates of application the compounds of formula I are distinguished by growth-inhibiting and herbicidal properties which make them excellent for use in crops of useful plants, especially cereals, cotton, soybeans, sunflowers, rape, maize and rice.

The compounds of formula I also have plant growth-regulating properties. The growth of both monocotyledons and dicotyledons is affected.

Inhibition of the vegetative growth makes it possible with many crop plants for the crop to be more densely planted, so that it is possible to achieve a higher yield per unit area of soil.

Another mechanism of the increase in yield when using growth regulators is based on the fact that the nutrients are used to the greater advantage of the formation of the flowers and fruit whilst the vegetative growth is restricted.

At suitable rates of application the compounds of formula I inhibit the new growth of grasses. This makes it possible to reduce the number of cuts necessary or to increase the intervals between cutting in grassed areas (parks, gardens, etc.). In an especially advantageous manner it is possible to use granulate formulations of the active ingredients of formula I for this purpose. Either the granulate may contain the active ingredient on its own, together with the customary adjuvants and carriers, or the active ingredient is formulated as a granulate together with a mineral fertiliser and/or, if desired, other active ingredients for controlling moss or other plant growth that is undesirable in grassed areas. Application in the form of a strewing granulate (for direct soil application) makes it possible, using equipment customary for maintaining grassed areas, to inhibit the new growth of grasses for a relatively long period. The granulate can be prepared in a manner known per se, and it preferably has a granule size of 0.1 to 2.0 mm, especially 0.25 to 1.0 mm.

As compounds that are effective in plant growth regulation there may be mentioned especially 2-[N-carbamoyl-N-(6-methyl-2-nitrophenyl)-amino]-4-trifluoromethyl-6-ethyl-pyrimidine and 2-[N-carbamoyl-N-(2-nitrophenyl)-amino]-4-trifluoromethyl-6-ethyl-pyrimidine.

At higher rates of application, weeds and grasses are damaged in their development to such an extent that they die.

In an especially advantageous manner, the growth-regulating compounds of formula I can be used for regulating the growth of intersown plants in maize crops.

Plants that are suitable in principle for intersowing in crops of maize are those that cover the soil between the individual maize plants and thus, especially, counteract soil erosion in maize crops.

Suitable plants for intersowing are, inter alia, rape, trefoil, grasses or leguminosae.

The invention relates also to herbicidal and plant growth-regulating compositions that contain an active ingredient of formula I, and to methods of controlling weeds pre-emergence and post-emergence and of influencing the growth of monocotyledonous and dicotyledonous plants, especially grasses, tropical cover crops and suckers.

The compounds of formula I are used in unmodified form or, preferably, in the form of compositions together with the adjuvants conventionally employed in the art of formulation, and are therefore advantageously formulated in known manner e.g. into emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The active substances of formula I can thus also be applied to mineral fertilisers (as a dressing). The composition so obtainable is advantageously suitable as a growth regulator for grasses.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surfaceactive compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids.

These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

Agglutinants are especially those adjuvants that in the case of granulation cause the carrier material, the adjuvants and the active ingredients to stick together, such as gum arabic or carboxymethylcellulose.

Surfactants customary in the art of formulation are described, inter alia, in the following publications:
"Mc Cutcheon's Detergents and Emulsifiers Annual"
MC Publishing Corp., Ridgewood, N. J., 1979.
Dr. Helmut Stache "Tensid Taschenbuch"
Carl Hanser Varlag, Munich/Vienna 1981.

The preparations usually contain 0.1 to 95%, preferably 0.1 to 80%, of a compound of formula I, 1 to 99.9% of a solid or liquid adjuvant, and 0 to 25%, preferably 0.1 to 25%, of a surfactant.

Preferred formulations are composed especially as follows: (%=percent by weight)

| Emulsifiable concentrates: | |
|---|---|
| a compound of formula I: | 1 to 20%, preferably 5 to 10% |
| surfactant: | 5 to 30%, preferably 10 to 20% |
| liquid carrier: | 50 to 94%, preferably 70 to 85%. |
| Dusts: | |
| a compound of formula I: | 0.1 to 10%, preferably 0.1 to 1% |
| solid carrier: | 99.9 to 90%, preferably 99.9 to 99%. |
| Suspension concentrates: | |
| a compound of formula I: | 5 to 75%, preferably 10 to 50% |
| water: | 94 to 25%, preferably 90 to 30% |
| surfactant: | 1 to 40%, preferably 2 to 30%. |
| Wettable powders: | |
| a compound of formula I: | 0.5 to 90%, preferably 1 to 80% |
| surfactant: | 0.5 to 20%, preferably 1 to 15% |
| solid carrier: | 5 to 95%, preferably 15 to 90%. |
| Granulates: | |
| a compound of formula I: | 0.5 to 30%, preferably 3 to 15% |
| solid carrier: | 99.5 to 70%, preferably 97 to 85%. |
| Strewing granulate: | |
| a compound of formula I: | 0.01 to 30%, preferably 0.05 to 15% |
| agglutinant: | 0.05 to 5%, preferably 0.1 to 2% |
| surfactant: | 0.5 to 20%, preferably 1 to 15% |
| solid carrier: | 99.44 to 45%, preferably 95 to 65%. |

Whereas commercial products will preferably be formulated as concentrates, the end user will normally employ dilute formulations. The formulations can be diluted to a concentration as low as 0.001% active ingredient. The rates of application are normally from 0.005 to 5 kg active ingredient/ha.

The compositions may also contain further additives such as stabilisers, antifoams, viscosity regulators, binders, tackifiers and also fertilisers or other active ingredients for obtaining special effects.

PREPARATION EXAMPLES

The (uncorrected) melting points in the following Preparation Examples are in ° C.

P. 1.1. Synthesis of
N-2-nitrophenyl-N-(4-methyl-6-pentafluoroethyl-pyrimidin-2-yl)-urea 104.1 g (0.3 mole) of 2-(2-nitrophenylamino)-4-methyl-6-pentafluoroethyl-pyrimidine are dissolved at 60° C. in 2.2 l of ethyl acetate and the solution is then cooled to 5° C.; 56.6 g (0.4 mole) of chlorosulfonyl isocyanate are added and the whole is stirred for 15 minutes at 5° C. Subsequently, 300 ml of cold water are poured in and the organic phase is separated off, dried with sodium sulfate and concentrated. The solid residue is triturated with a small amount of ethyl acetate.

73.9 g (63.2%) of the title compound of formula

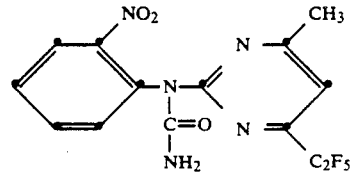

(Comp. No. 1.025) are isolated in the form of crystals having a melting point of 156° C.

P.1.2. Synthesis of
N-2-nitrophenyl-N-(4-methyl-6-pentafluoroethyl-pyrimidin-2-yl)-urea 21.5 g (0.05 mole) of N-(2-nitrophenylsulfonyl)-N'-(4-methyl-6-pentafluoroethyl-pyrimidin-2-yl)-urea are suspended in 100 ml of water and 200 ml of chloroform. At 25°, a solution of 3.2 g of sodium hydroxide in 350 ml of water is added dropwise to the suspension within a period of 4 hours. The two-phase solution is stirred for 16 hours. The CHCl₃ phase is then separated off, dried with sodium sulfate and concentrated by evaporation. The residue is recrystallised from chloroform.

4.0 g (20.7%) of the title compound of formula

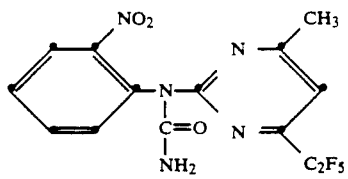

(Compound No. 1.025) are isolated in the form of crystals having a melting point of 156° C.

The compounds of formula I listed in the following Table 1 can be prepared analogously to Preparation Examples P.1.1. and P.1.2.

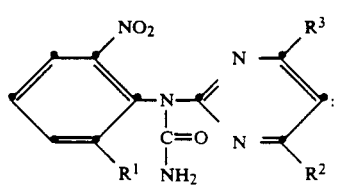

(I)

TABLE I

| Comp. No. | R¹ | R² | R³ | Physical data |
|---|---|---|---|---|
| 1.001 | H | CF₂Cl | CH₃ | m.p. 156° C. |
| 1.002 | H | CF₂Cl | C₂H₅ | |
| 1.003 | H | CF₂Cl | n-C₃H₇ | |
| 1.004 | H | CF₂Cl | i-C₃H₇ | m.p. 149–150° C. |
| 1.005 | H | CF₂Cl | sec-C₄H₉ | |
| 1.006 | H | CF₂Cl | i-C₄H₉ | |
| 1.007 | H | CHF₂ | CH₃ | m.p. 155–156° C. |
| 1.008 | H | CHF₂ | C₂H₅ | |
| 1.009 | H | CHF₂ | n-C₃H₇ | |
| 1.010 | H | CHF₂ | i-C₃H₇ | |
| 1.011 | H | CHF₂ | sec-C₄H₉ | |
| 1.012 | H | CHF₂ | i-C₄H₉ | |
| 1.013 | H | CF₂CCl₃ | CH₃ | |
| 1.014 | H | CF₂CCl₃ | C₂H₅ | |
| 1.015 | H | CF₂CCl₃ | n-C₃H₇ | |
| 1.016 | H | CF₂CCl₃ | i-C₃H₇ | |
| 1.017 | H | CF₂CCl₃ | sec-C₄H₉ | |
| 1.018 | H | CF₂CCl₃ | i-C₄H₉ | |
| 1.019 | H | CCl₂CF₃ | CH₃ | |
| 1.020 | H | CCl₂CF₃ | C₂H₅ | |
| 1.021 | H | CCl₂CF₃ | n-C₃H₇ | |
| 1.022 | H | CCl₂CF₃ | i-C₃H₇ | |
| 1.023 | H | CCl₂CF₃ | sec-C₄H₉ | |
| 1.024 | H | CCl₂CF₃ | i-C₄H₉ | |
| 1.025 | H | C₂F₅ | CH₃ | m.p. 156° C. |
| 1.026 | H | C₂F₅ | C₂H₅ | m.p. 156–157° C. |
| 1.027 | H | C₂F₅ | n-C₃H₇ | |
| 1.028 | H | C₂F₅ | i-C₃H₇ | m.p. 152–153° |
| 1.029 | H | C₂F₅ | sec-C₄H₉ | |
| 1.030 | H | C₂F₅ | i-C₄H₉ | |
| 1.031 | H | CF₂—CF₂Cl | CH₃ | |
| 1.032 | H | CF₂—CF₂Cl | C₂H₅ | |
| 1.033 | H | CF₂—CF₂Cl | n-C₃H₇ | |
| 1.034 | H | CF₂—CF₂Cl | i-C₃H₇ | |
| 1.035 | H | CF₂—CF₂Cl | sec-C₄H₉ | |
| 1.036 | H | CF₂—CF₂Cl | i-C₄H₉ | |
| 1.037 | H | CF₃ | C₂H₅ | m.p. 137–138° C. |
| 1.038 | H | CF₃ | i C₃H₇ | m.p. 150–151° C. |
| 1.039 | H | CF₃ | sec-C₄H₉ | m.p. 141–142° C. |
| 1.040 | H | CF₃ | i-C₄H₉ | |
| 1.041 | CH₃ | CF₂Cl | CH₃ | m.p. 178–179° C. |
| 1.042 | CH₃ | CF₂Cl | C₂H₅ | |
| 1.043 | CH₃ | CF₂Cl | n-C₃H₇ | |
| 1.044 | CH₃ | CF₂Cl | i-C₃H₇ | m.p. 153–154° C. |
| 1.045 | CH₃ | CF₂Cl | sec-C₄H₉ | |
| 1.046 | CH₃ | CF₂Cl | i-C₄H₉ | |
| 1.047 | CH₃ | CHF₂ | CH₃ | m.p. 158–160° C. |
| 1.048 | CH₃ | CHF₂ | C₂H₅ | |
| 1.049 | CH₃ | CHF₂ | n-C₃H₇ | |
| 1.050 | CH₃ | CHF₂ | i-C₃H₇ | |
| 1.051 | CH₃ | CHF₂ | sec-C₄H₉ | |
| 1.052 | CH₃ | CHF₂ | i-C₄H₉ | |
| 1.053 | CH₃ | CF₂CCl₃ | CH₃ | |
| 1.054 | CH₃ | CF₂CCl₃ | C₂H₅ | |
| 1.055 | CH₃ | CF₂CCl₃ | n-C₃H₇ | |
| 1.056 | CH₃ | CF₂CCl₃ | i-C₃H₇ | |
| 1.057 | CH₃ | CF₂CCl₃ | sec-C₄H₉ | |
| 1.058 | CH₃ | CF₂CCl₃ | i-C₄H₉ | |
| 1.059 | CH₃ | CCl₂CF₃ | CH₃ | |
| 1.060 | CH₃ | CCl₂CF₃ | C₂H₅ | |
| 1.061 | CH₃ | CCl₂CF₃ | n-C₃H₇ | |
| 1.062 | CH₃ | CCl₂CF₃ | i-C₃H₇ | |
| 1.063 | CH₃ | CCl₂CF₃ | sec-C₄H₉ | |
| 1.064 | CH₃ | CCl₂CF₃ | i-C₄H₉ | |
| 1.065 | CH₃ | C₂F₅ | CH₃ | |
| 1.066 | CH₃ | C₂F₅ | C₂H₅ | m.p. 135–136° C. |
| 1.067 | CH₃ | C₂F₅ | n-C₃H₇ | |
| 1.068 | CH₃ | C₂F₅ | i-C₃H₇ | m.p. 143–144° C. |
| 1.069 | CH₃ | C₂F₅ | sec-C₄H₉ | |
| 1.070 | CH₃ | C₂F₅ | i-C₄H₉ | |
| 1.071 | CH₃ | CF₂—CF₂Cl | CH₃ | |
| 1.072 | CH₃ | CF₂—CF₂Cl | C₂H₅ | |
| 1.073 | CH₃ | CF₂—CF₂Cl | n-C₃H₇ | |
| 1.074 | CH₃ | CF₂—CF₂Cl | i-C₃H₇ | |
| 1.075 | CH₃ | CF₂—CF₂Cl | sec-C₄H₉ | |
| 1.076 | CH₃ | CF₂—CF₂Cl | i-C₄H₉ | |
| 1.077 | CH₃ | CF₃ | C₂H₅ | m.p. 149–150° C. |
| 1.078 | CH₃ | CF₃ | i C₃H₇ | m.p. 135–138° C. |
| 1.079 | CH₃ | CF₃ | sec-C₄H₉ | m.p. 141–142° C. |
| 1.080 | CH₃ | CF₃ | i-C₄H₉ | |
| 1.081 | F | CF₂Cl | CH₃ | |
| 1.082 | F | CF₂Cl | C₂H₅ | |
| 1.083 | F | CF₂Cl | n-C₃H₇ | |
| 1.084 | F | CF₂Cl | i-C₃H₇ | |
| 1.085 | F | CF₂Cl | sec-C₄H₉ | |
| 1.086 | F | CF₂Cl | i-C₄H₉ | |
| 1.087 | F | CHF₂ | CH₃ | |
| 1.088 | F | CHF₂ | C₂H₅ | |
| 1.089 | F | CHF₂ | n-C₃H₇ | |
| 1.090 | F | CHF₂ | i-C₃H₇ | |
| 1.091 | F | CHF₂ | sec-C₄H₉ | |
| 1.092 | F | CHF₂ | i-C₄H₉ | |
| 1.093 | F | CF₂CCl₃ | CH₃ | |
| 1.094 | F | CF₂CCl₃ | C₂H₅ | |
| 1.095 | F | CF₂CCl₃ | n-C₃H₇ | |
| 1.096 | F | CF₂CCl₃ | i-C₃H₇ | |
| 1.097 | F | CF₂CCl₃ | sec-C₄H₉ | |
| 1.098 | F | CF₂CCl₃ | i-C₄H₉ | |
| 1.099 | F | CCl₂CF₃ | CH₃ | |
| 1.100 | F | CCl₂CF₃ | C₂H₅ | |
| 1.101 | F | CCl₂CF₃ | n-C₃H₇ | |
| 1.102 | F | CCl₂CF₃ | i-C₃H₇ | |
| 1.103 | F | CCl₂CF₃ | sec-C₄H₉ | |
| 1.104 | F | CCl₂CF₃ | i-C₄H₉ | |
| 1.105 | F | C₂F₅ | CH₃ | |
| 1.106 | F | C₂F₅ | C₂H₅ | m.p. 143–144° C. |
| 1.107 | F | C₂F₅ | n-C₃H₇ | |
| 1.108 | F | C₂F₅ | i-C₃H₇ | |
| 1.109 | F | C₂F₅ | sec-C₄H₉ | |
| 1.110 | F | C₂F₅ | i-C₄H₉ | |
| 1.111 | F | CF₂—CF₂Cl | CH₃ | |
| 1.112 | F | CF₂—CF₂Cl | C₂H₅ | |
| 1.113 | F | CF₂—CF₂Cl | n-C₃H₇ | |
| 1.114 | F | CF₂—CF₂Cl | i-C₃H₇ | |
| 1.115 | F | CF₂—CF₂Cl | sec-C₄H₉ | |
| 1.116 | F | CF₂—CF₂Cl | i-C₄H₉ | |
| 1.117 | F | CF₃ | C₂H₅ | m.p. 140–142° C. |
| 1.118 | F | CF₃ | i C₃H₇ | m.p. 145–146° C. |
| 1.119 | F | CF₃ | sec-C₄H₉ | |
| 1.120 | F | CF₃ | i-C₄H₉ | |
| 1.121 | Cl | CF₂Cl | CH₃ | |
| 1.122 | Cl | CF₂Cl | C₂H₅ | |
| 1.123 | Cl | CF₂Cl | n-C₃H₇ | |
| 1.124 | Cl | CF₂Cl | i-C₃H₇ | |
| 1.125 | Cl | CF₂Cl | sec-C₄H₉ | |
| 1.126 | Cl | CF₂Cl | i-C₄H₉ | |
| 1.127 | Cl | CHF₂ | CH₃ | |
| 1.128 | Cl | CHF₂ | C₂H₅ | |

TABLE I-continued

| Comp. No. | R¹ | R² | R³ | Physical data |
|---|---|---|---|---|
| 1.129 | Cl | $CHF_2$ | $n-C_3H_7$ | |
| 1.130 | Cl | $CHF_2$ | $i-C_3H_7$ | |
| 1.131 | Cl | $CHF_2$ | $sec-C_4H_9$ | |
| 1.132 | Cl | $CHF_2$ | $i-C_4H_9$ | |
| 1.133 | Cl | $CF_2CCl_3$ | $CH_3$ | |
| 1.134 | Cl | $CF_2CCl_3$ | $C_2H_5$ | |
| 1.135 | Cl | $CF_2CCl_3$ | $n-C_3H_7$ | |
| 1.136 | Cl | $CF_2CCl_3$ | $i-C_3H_7$ | |
| 1.137 | Cl | $CF_2CCl_3$ | $sec-C_4H_9$ | |
| 1.138 | Cl | $CF_2CCl_3$ | $i-C_4H_9$ | |
| 1.139 | Cl | $CCl_2CF_3$ | $CH_3$ | |
| 1.140 | Cl | $CCl_2CF_3$ | $C_2H_5$ | |
| 1.141 | Cl | $CCl_2CF_3$ | $n-C_3H_7$ | |
| 1.142 | Cl | $CCl_2CF_3$ | $i-C_3H_7$ | |
| 1.143 | Cl | $CCl_2CF_3$ | $sec-C_4H_9$ | |
| 1.144 | Cl | $CCl_2CF_3$ | $i-C_4H_9$ | |
| 1.145 | Cl | $C_2F_5$ | $CH_3$ | |
| 1.146 | Cl | $C_2F_5$ | $C_2H_5$ | |
| 1.147 | Cl | $C_2F_5$ | $n-C_3H_7$ | |
| 1.148 | Cl | $C_2F_5$ | $i-C_3H_7$ | |
| 1.149 | Cl | $C_2F_5$ | $sec-C_4H_9$ | |
| 1.150 | Cl | $C_2F_5$ | $i-C_4H_9$ | |
| 1.151 | Cl | $CF_2—CF_2Cl$ | $CH_3$ | |
| 1.152 | Cl | $CF_2—CF_2Cl$ | $C_2H_5$ | |
| 1.153 | Cl | $CF_2—CF_2Cl$ | $n-C_3H_7$ | |
| 1.154 | Cl | $CF_2—CF_2Cl$ | $i-C_3H_7$ | |
| 1.155 | Cl | $CF_2—CF_2Cl$ | $sec-C_4H_9$ | |
| 1.156 | Cl | $CF_2—CF_2Cl$ | $i-C_4H_9$ | |
| 1.157 | Cl | $CF_3$ | $C_2H_5$ | |
| 1.158 | Cl | $CF_3$ | $i C_3H_7$ | |
| 1.159 | Cl | $CF_3$ | $sec-C_4H_9$ | |
| 1.160 | Cl | $CF_3$ | $i-C_4H_9$ | |
| 1.161 | Br | $CF_2Cl$ | $CH_3$ | |
| 1.162 | Br | $CF_2Cl$ | $C_2H_5$ | |
| 1.163 | Br | $CF_2Cl$ | $n-C_3H_7$ | |
| 1.164 | Br | $CF_2Cl$ | $i-C_3H_7$ | |
| 1.165 | Br | $CF_2Cl$ | $sec-C_4H_9$ | |
| 1.166 | Br | $CF_2Cl$ | $i-C_4H_9$ | |
| 1.167 | Br | $CHF_2$ | $CH_3$ | |
| 1.168 | Br | $CHF_2$ | $C_2H_5$ | |
| 1.169 | Br | $CHF_2$ | $n-C_3H_7$ | |
| 1.170 | Br | $CHF_2$ | $i-C_3H_7$ | |
| 1.171 | Br | $CHF_2$ | $sec-C_4H_9$ | |
| 1.172 | Br | $CHF_2$ | $i-C_4H_9$ | |
| 1.173 | Br | $CF_2CCl_3$ | $CH_3$ | |
| 1.174 | Br | $CF_2CCl_3$ | $C_2H_5$ | |
| 1.175 | Br | $CF_2CCl_3$ | $n-C_3H_7$ | |
| 1.176 | Br | $CF_2CCl_3$ | $i-C_3H_7$ | |
| 1.177 | Br | $CF_2CCl_3$ | $sec-C_4H_9$ | |
| 1.178 | Br | $CF_2CCl_3$ | $i-C_4H_9$ | |
| 1.179 | Br | $CCl_2CF_3$ | $CH_3$ | |
| 1.180 | Br | $CCl_2CF_3$ | $C_2H_5$ | |
| 1.181 | Br | $CCl_2CF_3$ | $n-C_3H_7$ | |
| 1.182 | Br | $CCl_2CF_3$ | $i-C_3H_7$ | |
| 1.183 | Br | $CCl_2CF_3$ | $sec-C_4H_9$ | |
| 1.184 | Br | $CCl_2CF_3$ | $i-C_4H_9$ | |
| 1.185 | Br | $C_2F_5$ | $CH_3$ | |
| 1.186 | Br | $C_2F_5$ | $C_2H_5$ | |
| 1.187 | Br | $C_2F_5$ | $n-C_3H_7$ | |
| 1.188 | Br | $C_2F_5$ | $i-C_3H_7$ | |
| 1.189 | Br | $C_2F_5$ | $sec-C_4H_9$ | |
| 1.190 | Br | $C_2F_5$ | $i-C_4H_9$ | |
| 1.191 | Br | $CF_2—CF_2Cl$ | $CH_3$ | |
| 1.192 | Br | $CF_2—CF_2Cl$ | $C_2H_5$ | |
| 1.193 | Br | $CF_2—CF_2Cl$ | $n-C_3H_7$ | |
| 1.194 | Br | $CF_2—CF_2Cl$ | $i-C_3H_7$ | |
| 1.195 | Br | $CF_2—CF_2Cl$ | $sec-C_4H_9$ | |
| 1.196 | Br | $CF_2—CF_2Cl$ | $i-C_4H_9$ | |
| 1.197 | Br | $CF_3$ | $C_2H_5$ | |
| 1.198 | Br | $CF_3$ | $i C_3H_7$ | |
| 1.199 | Br | $CF_3$ | $sec-C_4H_9$ | |
| 1.200 | Br | $CF_3$ | $i-C_4H_9$ | |
| 1.201 | H | $CF_3$ | $n-C_3H_7$ | m.p. 138–139° C. |
| 1.202 | $CH_3$ | $CF_3$ | $n-C_3H_7$ | m.p. 136–137° C. |
| 1.203 | F | $CF_3$ | $n-C_3H_7$ | |
| 1.204 | Cl | $CF_3$ | $n-C_3H_7$ | |
| 1.205 | Br | $CF_3$ | $n-C_3H_7$ | |

P.2.1. Synthesis of 2-(2-nitrophenylamino)-4-methyl-6-pentafluoroethyl-pyrimidine 121 g (0.5 mole) of 2-nitrophenyl-guanidine-carbonate, 140 g of 5,5,6,6,6-pentafluorohexane-2,4-dione and 200 ml of diethyl glycol dimethyl ether are first heated to 65° C. and, when the evolution of CO2 has ceased, are then heated to 140° C. The water freed during condensation is distilled off. After 3½ hours the suspension is cooled, water is added and the pH is adjusted to 4–5 with concentrated hydrochloric acid. The yellow precipitate is filtered off, washed with water and dried in vacuo at 80° C.

110.5 g (63.7%) of the title compound of formula

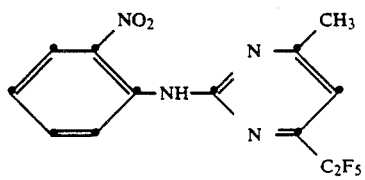

(Comp. No. 2.025) are isolated in the form of crystals having a melting point of 82°–83° C.

The compounds of formula II

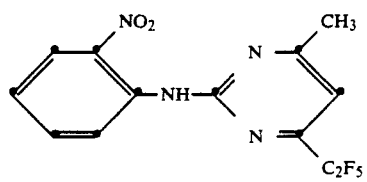

listed in the Table 2 can be prepared analogously to Preparation Example P.2.1.

TABLE 2

| Comp. No. | R¹ | R² | R³ | Physical data |
|---|---|---|---|---|
| 2.001 | H | $CF_2Cl$ | $CH_3$ | m.p. 127–128° C. |
| 2.002 | H | $CF_2Cl$ | $C_2H_5$ | |
| 2.003 | H | $CF_2Cl$ | $n-C_3H_7$ | |
| 2.004 | H | $CF_2Cl$ | $i-C_3H_7$ | m.p. 52–54° C. |
| 2.005 | H | $CF_2Cl$ | $sec-C_4H_9$ | |
| 2.006 | H | $CF_2Cl$ | $i-C_4H_9$ | |
| 2.007 | H | $CHF_2$ | $CH_3$ | m.p. 143–144° C. |
| 2.008 | H | $CHF_2$ | $C_2H_5$ | |
| 2.009 | H | $CHF_2$ | $n-C_3H_7$ | |
| 2.010 | H | $CHF_2$ | $i-C_3H_7$ | |
| 2.011 | H | $CHF_2$ | $sec-C_4H_9$ | |
| 2.012 | H | $CHF_2$ | $i-C_4H_9$ | |
| 2.013 | H | $CF_2CCl_3$ | $CH_3$ | |
| 2.014 | H | $CF_2CCl_3$ | $C_2H_5$ | |
| 2.015 | H | $CF_2CCl_3$ | $n-C_3H_7$ | |
| 2.016 | H | $CF_2CCl_3$ | $i-C_3H_7$ | |
| 2.017 | H | $CF_2CCl_3$ | $sec-C_4H_9$ | |
| 2.018 | H | $CF_2CCl_3$ | $i-C_4H_9$ | |
| 2.019 | H | $CCl_2CF_3$ | $CH_3$ | |
| 2.020 | H | $CCl_2CF_3$ | $C_2H_5$ | |
| 2.021 | H | $CCl_2CF_3$ | $n-C_3H_7$ | |
| 2.022 | H | $CCl_2CF_3$ | $i-C_3H_7$ | |
| 2.023 | H | $CCl_2CF_3$ | $sec-C_4H_9$ | |
| 2.024 | H | $CCl_2CF_3$ | $i-C_4H_9$ | |
| 2.025 | H | $C_2F_5$ | $CH_3$ | m.p. 82–83° C. |
| 2.026 | H | $C_2F_5$ | $C_2H_5$ | m.p. 82–83° C. |
| 2.027 | H | $C_2F_5$ | $n-C_3H_7$ | |
| 2.028 | H | $C_2F_5$ | $i-C_3H_7$ | m.p. 64–65° C. |
| 2.029 | H | $C_2F_5$ | $sec-C_4H_9$ | |
| 2.030 | H | $C_2F_5$ | $i-C_4H_9$ | |
| 2.031 | H | $CF_2—CF_2Cl$ | $CH_3$ | |
| 2.032 | H | $CF_2—CF_2Cl$ | $C_2H_5$ | |
| 2.033 | H | $CF_2—CF_2Cl$ | $n-C_3H_7$ | |
| 2.034 | H | $CF_2—CF_2Cl$ | $i-C_3H_7$ | |

TABLE 2-continued

| Comp. No. | $R^1$ | $R^2$ | $R^3$ | Physical data |
|---|---|---|---|---|
| 2.035 | H | $CF_2-CF_2Cl$ | sec-$C_4H_9$ | |
| 2.036 | H | $CF_2-CF_2Cl$ | i-$C_4H_9$ | |
| 2.037 | H | $CF_3$ | $C_2H_5$ | m.p. 71–72° C. |
| 2.038 | H | $CF_3$ | i $C_3H_7$ | m.p. 72–73° C. |
| 2.039 | H | $CF_3$ | sec-$C_4H_9$ | $N_D^{25}$ 1.5730 |
| 2.040 | H | $CF_3$ | i-$C_4H_9$ | |
| 2.041 | $CH_3$ | $CF_2Cl$ | $CH_3$ | m.p. 96–97° C. |
| 2.042 | $CH_3$ | $CF_2Cl$ | $C_2H_5$ | |
| 2.043 | $CH_3$ | $CF_2Cl$ | n-$C_3H_7$ | |
| 2.044 | $CH_3$ | $CF_2Cl$ | i-$C_3H_7$ | m.p. 67–69° C. |
| 2.045 | $CH_3$ | $CF_2Cl$ | sec-$C_4H_9$ | |
| 2.046 | $CH_3$ | $CF_2Cl$ | i-$C_4H_9$ | |
| 2.047 | $CH_3$ | $CHF_2$ | $CH_3$ | m.p. 126–127° C. |
| 2.048 | $CH_3$ | $CHF_2$ | $C_2H_5$ | |
| 2.049 | $CH_3$ | $CHF_2$ | n-$C_3H_7$ | |
| 2.050 | $CH_3$ | $CHF_2$ | i-$C_3H_7$ | |
| 2.051 | $CH_3$ | $CHF_2$ | sec-$C_4H_9$ | |
| 2.052 | $CH_3$ | $CHF_2$ | i-$C_4H_9$ | |
| 2.053 | $CH_3$ | $CF_2CCl_3$ | $CH_3$ | |
| 2.054 | $CH_3$ | $CF_2CCl_3$ | $C_2H_5$ | |
| 2.055 | $CH_3$ | $CF_2CCl_3$ | n-$C_3H_7$ | |
| 2.056 | $CH_3$ | $CF_2CCl_3$ | i-$C_3H_7$ | |
| 2.057 | $CH_3$ | $CF_2CCl_3$ | sec-$C_4H_9$ | |
| 2.058 | $CH_3$ | $CF_2CCl_3$ | i-$C_4H_9$ | |
| 2.059 | $CH_3$ | $CCl_2CF_3$ | $CH_3$ | |
| 2.060 | $CH_3$ | $CCl_2CF_3$ | $C_2H_5$ | |
| 2.061 | $CH_3$ | $CCl_2CF_3$ | n-$C_3H_7$ | |
| 2.062 | $CH_3$ | $CCl_2CF_3$ | i-$C_3H_7$ | |
| 2.063 | $CH_3$ | $CCl_2CF_3$ | sec-$C_4H_9$ | |
| 2.064 | $CH_3$ | $CCl_2CF_3$ | i-$C_4H_9$ | |
| 2.065 | $CH_3$ | $C_2F_5$ | $CH_3$ | |
| 2.066 | $CH_3$ | $C_2F_5$ | $C_2H_5$ | m.p. 87–88° C. |
| 2.067 | $CH_3$ | $C_2F_5$ | n-$C_3H_7$ | |
| 2.068 | $CH_3$ | $C_2F_5$ | i-$C_3H_7$ | m.p. 50–51° C. |
| 2.069 | $CH_3$ | $C_2F_5$ | sec-$C_4H_9$ | |
| 2.070 | $CH_3$ | $C_2F_5$ | i-$C_4H_9$ | |
| 2.071 | $CH_3$ | $CF_2-CF_2Cl$ | $CH_3$ | |
| 2.072 | $CH_3$ | $CF_2-CF_2Cl$ | $C_2H_5$ | |
| 2.073 | $CH_3$ | $CF_2-CF_2Cl$ | n-$C_3H_7$ | |
| 2.074 | $CH_3$ | $CF_2-CF_2Cl$ | i-$C_3H_7$ | |
| 2.075 | $CH_3$ | $CF_2-CF_2Cl$ | sec-$C_4H_9$ | |
| 2.076 | $CH_3$ | $CF_2-CF_2Cl$ | i-$C_4H_9$ | |
| 2.077 | $CH_3$ | $CF_3$ | $C_2H_5$ | m.p. 84–85° C. |
| 2.078 | $CH_3$ | $CF_3$ | i $C_3H_7$ | $n_D^{30}$: 1,5382 |
| 2.079 | $CH_3$ | $CF_3$ | sec-$C_4H_9$ | $n_D^{25}$: 1,5318 |
| 2.080 | $CH_3$ | $CF_3$ | i-$C_4H_9$ | |
| 2.081 | F | $CF_2Cl$ | $CH_3$ | |
| 2.082 | F | $CF_2Cl$ | $C_2H_5$ | |
| 2.083 | F | $CF_2Cl$ | n-$C_3H_7$ | |
| 2.084 | F | $CF_2Cl$ | i-$C_3H_7$ | |
| 2.085 | F | $CF_2Cl$ | sec-$C_4H_9$ | |
| 2.086 | F | $CF_2Cl$ | i-$C_4H_9$ | |
| 2.087 | F | $CHF_2$ | $CH_3$ | |
| 2.088 | F | $CHF_2$ | $C_2H_5$ | |
| 2.089 | F | $CHF_2$ | n-$C_3H_7$ | |
| 2.090 | F | $CHF_2$ | i-$C_3H_7$ | |
| 2.091 | F | $CHF_2$ | sec-$C_4H_9$ | |
| 2.092 | F | $CHF_2$ | i-$C_4H_9$ | |
| 2.093 | F | $CF_2CCl_3$ | $CH_3$ | |
| 2.094 | F | $CF_2CCl_3$ | $C_2H_5$ | |
| 2.095 | F | $CF_2CCl_3$ | n-$C_3H_7$ | |
| 2.096 | F | $CF_2CCl_3$ | i-$C_3H_7$ | |
| 2.097 | F | $CF_2CCl_3$ | sec-$C_4H_9$ | |
| 2.098 | F | $CF_2CCl_3$ | i-$C_4H_9$ | |
| 2.099 | F | $CCl_2CF_3$ | $CH_3$ | |
| 2.100 | F | $CCl_2CF_3$ | $C_2H_5$ | |
| 2.101 | F | $CCl_2CF_3$ | n-$C_3H_7$ | |
| 2.102 | F | $CCl_2CF_3$ | i-$C_3H_7$ | |
| 2.103 | F | $CCl_2CF_3$ | sec-$C_4H_9$ | |
| 2.104 | F | $CCl_2CF_3$ | i-$C_4H_9$ | |
| 2.105 | F | $C_2F_5$ | $CH_3$ | |
| 2.106 | F | $C_2F_5$ | $C_2H_5$ | m.p. 63–65° C. |
| 2.107 | F | $C_2F_5$ | n-$C_3H_7$ | |
| 2.108 | F | $C_2F_5$ | i-$C_3H_7$ | |
| 2.109 | F | $C_2F_5$ | sec-$C_4H_9$ | |
| 2.110 | F | $C_2F_5$ | i-$C_4H_9$ | |
| 2.111 | F | $CF_2-CF_2Cl$ | $CH_3$ | |
| 2.112 | F | $CF_2-CF_2Cl$ | $C_2H_5$ | |
| 2.113 | F | $CF_2-CF_2Cl$ | n-$C_3H_7$ | |
| 2.114 | F | $CF_2-CF_2Cl$ | i-$C_3H_7$ | |
| 2.115 | F | $CF_2-CF_2Cl$ | sec-$C_4H_9$ | |
| 2.116 | F | $CF_2-CF_2Cl$ | i-$C_4H_9$ | |
| 2.117 | F | $CF_3$ | $C_2H_5$ | m.p. 89–91° C. |
| 2.118 | F | $CF_3$ | i $C_3H_7$ | $n_D^{30}$: 1,5313 |
| 2.119 | F | $CF_3$ | sec-$C_4H_9$ | |
| 2.120 | F | $CF_3$ | i-$C_4H_9$ | |
| 2.121 | Cl | $CF_2Cl$ | $CH_3$ | |
| 2.122 | Cl | $CF_2Cl$ | $C_2H_5$ | |
| 2.123 | Cl | $CF_2Cl$ | n-$C_3H_7$ | |
| 2.124 | Cl | $CF_2Cl$ | i-$C_3H_7$ | |
| 2.125 | Cl | $CF_2Cl$ | sec-$C_4H_9$ | |
| 2.126 | Cl | $CF_2Cl$ | i-$C_4H_9$ | |
| 2.127 | Cl | $CHF_2$ | $CH_3$ | |
| 2.128 | Cl | $CHF_2$ | $C_2H_5$ | |
| 2.129 | Cl | $CHF_2$ | n-$C_3H_7$ | |
| 2.130 | Cl | $CHF_2$ | i-$C_3H_7$ | |
| 2.131 | Cl | $CHF_2$ | sec-$C_4H_9$ | |
| 2.132 | Cl | $CHF_2$ | i-$C_4H_9$ | |
| 2.133 | Cl | $CF_2CCl_3$ | $CH_3$ | |
| 2.134 | Cl | $CF_2CCl_3$ | $C_2H_5$ | |
| 2.135 | Cl | $CF_2CCl_3$ | n-$C_3H_7$ | |
| 2.136 | Cl | $CF_2CCl_3$ | i-$C_3H_7$ | |
| 2.137 | Cl | $CF_2CCl_3$ | sec-$C_4H_9$ | |
| 2.138 | Cl | $CF_2CCl_3$ | i-$C_4H_9$ | |
| 2.139 | Cl | $CCl_2CF_3$ | $CH_3$ | |
| 2.140 | Cl | $CCl_2CF_3$ | $C_2H_5$ | |
| 2.141 | Cl | $CCl_2CF_3$ | n-$C_3H_7$ | |
| 2.142 | Cl | $CCl_2CF_3$ | i-$C_3H_7$ | |
| 2.143 | Cl | $CCl_2CF_3$ | sec-$C_4H_9$ | |
| 2.144 | Cl | $CCl_2CF_3$ | i-$C_4H_9$ | |
| 2.145 | Cl | $C_2F_5$ | $CH_3$ | |
| 2.146 | Cl | $C_2F_5$ | $C_2H_5$ | |
| 2.147 | Cl | $C_2F_5$ | n-$C_3H_7$ | |
| 2.148 | Cl | $C_2F_5$ | i-$C_3H_7$ | |
| 2.149 | Cl | $C_2F_5$ | sec-$C_4H_9$ | |
| 2.150 | Cl | $C_2F_5$ | i-$C_4H_9$ | |
| 2.151 | Cl | $CF_2-CF_2Cl$ | $CH_3$ | |
| 2.152 | Cl | $CF_2-CF_2Cl$ | $C_2H_5$ | |
| 2.153 | Cl | $CF_2-CF_2Cl$ | n-$C_3H_7$ | |
| 2.154 | Cl | $CF_2-CF_2Cl$ | i-$C_3H_7$ | |
| 2.155 | Cl | $CF_2-CF_2Cl$ | sec-$C_4H_9$ | |
| 2.156 | Cl | $CF_2-CF_2Cl$ | i-$C_4H_9$ | |
| 2.157 | Cl | $CF_3$ | $C_2H_5$ | |
| 2.158 | Cl | $CF_3$ | i $C_3H_7$ | |
| 2.159 | Cl | $CF_3$ | sec-$C_4H_9$ | |
| 2.160 | Cl | $CF_3$ | i-$C_4H_9$ | |
| 2.161 | Br | $CF_2Cl$ | $CH_3$ | |
| 2.162 | Br | $CF_2Cl$ | $C_2H_5$ | |
| 2.163 | Br | $CF_2Cl$ | n-$C_3H_7$ | |
| 2.164 | Br | $CF_2Cl$ | i-$C_3H_7$ | |
| 2.165 | Br | $CF_2Cl$ | sec-$C_4H_9$ | |
| 2.166 | Br | $CF_2Cl$ | i-$C_4H_9$ | |
| 2.167 | Br | $CHF_2$ | $CH_3$ | |
| 2.168 | Br | $CHF_2$ | $C_2H_5$ | |
| 2.169 | Br | $CHF_2$ | n-$C_3H_7$ | |
| 2.170 | Br | $CHF_2$ | i-$C_3H_7$ | |
| 2.171 | Br | $CHF_2$ | sec-$C_4H_9$ | |
| 2.172 | Br | $CHF_2$ | i-$C_4H_9$ | |
| 2.173 | Br | $CF_2CCl_3$ | $CH_3$ | |
| 2.174 | Br | $CF_2CCl_3$ | $C_2H_5$ | |
| 2.175 | Br | $CF_2CCl_3$ | n-$C_3H_7$ | |
| 2.176 | Br | $CF_2CCl_3$ | i-$C_3H_7$ | |
| 2.177 | Br | $CF_2CCl_3$ | sec-$C_4H_9$ | |
| 2.178 | Br | $CF_2CCl_3$ | i-$C_4H_9$ | |
| 2.179 | Br | $CCl_2CF_3$ | $CH_3$ | |
| 2.180 | Br | $CCl_2CF_3$ | $C_2H_5$ | |
| 2.181 | Br | $CCl_2CF_3$ | n-$C_3H_7$ | |
| 2.182 | Br | $CCl_2CF_3$ | i-$C_3H_7$ | |
| 2.183 | Br | $CCl_2CF_3$ | sec-$C_4H_9$ | |
| 2.184 | Br | $CCl_2CF_3$ | i-$C_4H_9$ | |
| 2.185 | Br | $C_2F_5$ | $CH_3$ | |
| 2.186 | Br | $C_2F_5$ | $C_2H_5$ | |
| 2.187 | Br | $C_2F_5$ | n-$C_3H_7$ | |
| 2.188 | Br | $C_2F_5$ | i-$C_3H_7$ | |
| 2.189 | Br | $C_2F_5$ | sec-$C_4H_9$ | |
| 2.190 | Br | $C_2F_5$ | i-$C_4H_9$ | |
| 2.191 | Br | $CF_2-CF_2Cl$ | $CH_3$ | |
| 2.192 | Br | $CF_2-CF_2Cl$ | $C_2H_5$ | |
| 2.193 | Br | $CF_2-CF_2Cl$ | n-$C_3H_7$ | |
| 2.194 | Br | $CF_2-CF_2Cl$ | i-$C_3H_7$ | |
| 2.195 | Br | $CF_2-CF_2Cl$ | sec-$C_4H_9$ | |
| 2.196 | Br | $CF_2-CF_2Cl$ | i-$C_4H_9$ | |

TABLE 2-continued

| Comp. No. | R¹ | R² | R³ | Physical data |
|---|---|---|---|---|
| 2.197 | Br | CF₃ | C₂H₅ | |
| 2.198 | Br | CF₃ | i C₃H₇ | |
| 2.199 | Br | CF₃ | sec-C₄H₉ | |
| 2.200 | Br | CF₃ | i-C₄H₉ | |
| 2.201 | H | CF₃ | n-C₃H₇ | m.p. 61–62° C. |
| 2.202 | CH₃ | CF₃ | n-C₃H₇ | $n_D^{25}$: 1,5425 |
| 2.203 | F | CF₃ | n-C₃H₇ | |
| 2.204 | Cl | CF₃ | n-C₃H₇ | |
| 2.205 | Br | CF₃ | n-C₃H₇ | |

BIOLOGICAL EXAMPLES

Example B1

Pre-emergence herbicidal action

In a greenhouse, immediately after sowing the test plants in seed trays the surface of the soil is treated with an aqueous spray mixture corresponding to a rate of application of 4 kg of active ingredient/hectare. The seed trays are kept in the greenhouse at 22°–25° C. and 50–70% relative humidity.

After 3 weeks the herbicidal action is assessed in comparison with an untreated control group using a nine-stage evaluation scale (1=total damage, 9=no effect).

Ratings of 1 to 4 (especially 1 to 3) indicate a good to very good herbicidal action.

In this test the following compounds of formula I show good to very good herbicidal activity against the weeds Setaria and Stellaria: Compound nos.: 1.001, 1.004, 1.007, 1.025, 1.026, 1.028, 1.037, 1.038, 1.039, 1.041, 1.044, 1.047, 1.066, 1.077, 1.078, 1.079, 1.117, 1.118, 1.201 und 1.202.

Example B2

Herbicidal action in transplanted rice

Water weeds are sown in plastic beakers (425 cm² surface area, 5.0 l volume). To this rice is transplanted at the three foliar stage. After sowing and transplantation the beakers are filled to the soil surface with water. 3 days after sowing and transplantation the water level is raised slightly above (3–5 mm) the surface of the soil. The application of the test substance is done three days after sowing and transplantation at an application rate of 1000 and 500 g/ha by injecting an aqueous emulsion into the water (the application volume corresponds to 1400 l/ha). The plant beakers are then placed in a greenhouse under optimum growth conditions for the rice and the weeds, i.e. 25°–30° C. and high humidity.

The test is evaluated three weeks after application in comparison with an untreated control using a nine-stage evaluation scale.

Ratings of 1 to 4 (especially 1 to 3) indicate good to very good herbicidal action. Ratings of 6 to 9 (especially 7 to 9) indicate a good tolerance (especially in rice).

In this test following compound of formula I show good herbicidal action against Echinochloa crus galli and good tolerance to the rice: Compounds nos.: 1.001, 1.037 and 1.047.

Example B3

Post-emergence herbicidal action (selective herbicidal action)

Immediately after the test plants have been sawn into beakers with 12 to 15 cm diameter the covering soil was treated with an aqueous formulation containing the active ingredient according to an application rate of 1000 and 500 [g] AS/[ha].

The beakers were kept in a greenhouse at temperatures between 22 and 25° C. and a rel. humidity of 50 to 70%.

After 3 weeks the herbicidal action is assessed in comparison with an untreated control group using a nine-stage evaluation scale (1=total damage, 9=no effect).

Ratings of 1 to 4 (especially 1 to 3) indicate a good to very good herbicidal action. Ratings of 6 to 9 (especially 7 to 9) indicate a good tolerance (especially in case of crop plants).

In this test the following compounds of formula I show good to very good herbicidal action inter alia against the weeds named hereinafter: Digitaria sang., Echinochloa crus galli, Sorghum halep., Chemopodium Sp., Chrysanthenum leuc., Galium aparine, Viola tricolor and Veronica Sp.: 1.007, 1.025, 1.037, 1.038, 1.041 and 1.106.

Additionally compounds 1.007, 1.025, 1.037 and 1.038 have good to very good herbicidal action inter alia against Lolium perenne, Alopecurus myos., Abutilon, Chenopodium Sp., Solanum nigrum and Stellaria. The compounds named above show inter alia good to very good tolerance in barley, maize, soya, cotton, sunflowers or rape.

Example B4

Growth inhibition in cereals

The plants (for example summer barley of the Iban variety) are sown in 15 cm plastics pots containing sterile soil and cultivated in a climatic chamber at a daytime temperature of 10°–15° C. and a night time temperature of 5°–10° C. The illumination time is 13.5 hours per day.

Approximately 34 days after sowing and after thinning out to 4 plants per pot, 0.3 to 3 kg of active ingredient/ha, generally as a 25% strength formulation in an aqueous spray mixture, are applied. The amount of water applied is approximately 500 l/ha. After the application the plants are placed in a greenhouse at a daytime temperature of at least 10° C. The illumination time is at least 13.5 hours/day.

The evaluation is carried out approximately 28 days after the treatment. At this point the height of the new growth is measured.

The compounds of formula 1 tested cause a reduction in new growth compared with the untreated control.

Example B5

Growth inhibition in grasses with trefoil

A mixture of grasses (for example Poa, Festuca, Lolium, Bromus, Cynosurus) and trefoil (Trifolium pratenese/repens) is sown in 15 cm plastics pots containing sterile soil and cultivated in a greenhouse at a daytime temperature of 21° C. and a night time temperature of 17° C. The illumination time is 13.5 hours/day at a light intensity of at least 7000 Lux. After emergence the plants are cut back weekly to a height of approximately 6 cm. Approximately 42 days after sowing and 1 day after the last cut, 0.3 to 3 kg of active ingredient/hectare are applied, generally as a 25% strength formulation in an aqueous spray mixture. The amount of water applied is approximately 500 l/ha.

Evaluation is carried out approximately 3 weeks after the treatment. At this point the height of the new growth is measured.

The compounds of formula I tested cause a reduction in new growth compared with the untreated control.

Example B6

Growth inhibition in cereals *Hordeum vulgare* (summer barley) and *Secale* (summer rye) are sown according to cereal type in plastics pots containing sterilised soil in a greenhouse and watered as required. Approximately 21 days after sowing, the seedlings are sprayed with an aqueous spray mixture of an active ingredient from Table 1. 21 days after the application the growth of the cereal is assessed. The treated plants exhibit a reduction in new growth compared with untreated controls as well as, in some cases, an increase in stalk diameter.

Example B7

Growth inhibition in grasses

The grasses *Lolium perenne*, *Poa pratensis*, *Festuca ovina*, *Dactylis glomerata* and *Cynodon dactylon* are sown in a greenhouse in plastics trays containing a soil/peat/sand mixture (6:3:1) and watered as required. The emerged grasses are cut back weekly to a height of 4 cm and, about 50 days after sowing and one day after the last cut, are sprayed with an aqueous spray mixture of an active ingredient from Table 1. The quantity of active ingredient is equivalent to up to 500 g of active ingredient per hectare. 21 days after application, the growth of the grasses is assessed.

The compounds of Table 1 tested cause a reduction in the new growth compared with the untreated control.

Formulation Examples

Example F1

Formulation Examples for active ingredients of formula I, (throughout, percentages are by weight)

| (a) Emulsifiable concentrates | (a) | (b) | (c) |
| --- | --- | --- | --- |
| a compound from Table 1 | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any desired concentration can be produced from such concentrates by dilution with water.

| (b) Solutions | (a) | (b) | (c) |
| --- | --- | --- | --- |
| a compound from Table 1 | 80% | 10% | 5% |
| ethylene glycol monomethyl ether | 20% | — | — |
| polyethylene glycol MW 400 | — | 70% | — |
| N-methyl-2-pyrrolidone | — | 20% | 5% |
| epoxidised coconut oil | — | — | 90% |

These solutions are suitable for application in the form of micro-drops.

| (c) Granulates | (a) | (b) |
| --- | --- | --- |
| a compound from Table 1 | 5% | 10% |
| kaolin | 94% | — |
| highly dispersed silicic acid | 1% | — |
| attapulgite | — | 90% |

A solution of the active ingredient is sprayed onto the carrier, and the solvent is subsequently evaporated off in vacuo.

| (d) Dusts | (a) | (b) |
| --- | --- | --- |
| a compound from Table 1 | 2% | 5% |
| highly dispersed silicic acid | 1% | 5% |
| talcum | 97% | — |
| kaolin | — | 90% |

Ready-for-use dusts are obtained by homogeneously mixing the carriers with the active ingredient.

| (e) Wettable powders | (a) | (b) |
| --- | --- | --- |
| a compound from Table 1 | 20% | 60% |
| sodium lignosulfonate | 5% | 5% |
| sodium lauryl sulfate | — | 6% |
| octylphenol polyethylene glycol ether (7-8 moles of ethylene oxide) | — | 2% |
| highly dispersed silicic acid | 5% | 27% |
| kaolin | 70% | — |

The active ingredient is thoroughly mixed with the adjuvants and the mixture is thoroughly ground in a suitable mill, affording wettable powders which can be diluted with water to give suspensions of the desired concentration.

| (f) Extruder granulate | |
| --- | --- |
| a compound from Table 1 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| (g) Coated granulate | |
| --- | --- |
| a compound from Table 1 | 3% |
| polyethylene glycol (MW 200) | 3% |
| kaolin | 94% |

The finely ground active ingredient is uniformly applied, in a mixer, to the kaolin moistened with polyethylene glycol. Non-dusty coated granulates are obtained in this manner.

| (h) Suspension concentrate | |
| --- | --- |
| a compound from Table 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | ad 100% |

What is claimed is:

1. A compound of formula I

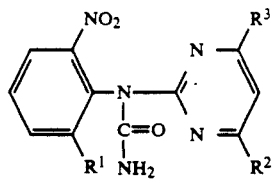

in which
R$^1$ is hydrogen, methyl, fluorine, chlorine or bromine,
R$^2$ is C$_1$-C$_2$haloalkyl having at least 2 fluorine atoms, and
R$^3$ is C$_1$-C$_4$alkyl,
with the proviso that R$^2$ is not trifluoromethyl when R$^3$ is methyl, or a salt or addition compound of formula I with an acid, base or complex former.

2. A compound of formula I according to claim 1, in which
R$^1$ is hydrogen, methyl, fluorine, chlorine or bromine,
R$^2$ is chlorodifluoromethyl, difluoromethyl, 1,1-difluoro-2,2,2-trichloroethyl, 1,1-dichloro-2,2,2-trifluoroethyl, pentafluoroethyl, 1,1,2,2-tetrafluoro-2-chloroethyl or trifluoromethyl and
R$^3$ is C$_1$-C$_4$alkyl.

3. A compound of formula I according to claim 1, in which
R$^1$ is hydrogen, methyl, fluorine, chlorine or bromine,
R$^2$ is chlorodifluoromethyl, difluoromethyl, 1,1-difluoro-2,2,2-trichloroethyl, 1,1-dichloro-2,2,2-trifluoroethyl, pentafluoroethyl, 1,1,2,2-tetrafluoro-2-chloroethyl or trifluoromethyl and
R$^3$ is methyl, ethyl, n-propyl, isopropyl, sec.-butyl or isobutyl.

4. A compound of formula I according to claim 1, in which
R$^1$ is hydrogen or methyl,
R$^2$ is trifluoromethyl and
R$^3$ is methyl, ethyl or isopropyl.

5. 2[N-carbamoyl-N-(6-methyl-2-nitrophenyl)-amino]-4-trifluoromethyl-6-ethyl-pyrimidine or 2-[N-carbamoyl-N-(2-nitrophenyl)-amino]-4-trifluoromethyl-6-ethyl-pyrimidine according to claim 4.

6. A herbicidal composition which comprises as active ingredient a herbicidally effective amount of a compound according to claim 1, together with an agrochemically acceptable carrier or other adjuvant.

7. A plant growth-regulating composition which comprises as active ingredient a growth-regulatingly effective amount of a compound according to claim 1, together with an agrochemically acceptable carrier or other adjuvant.

8. A plant growth-regulating composition according to claim 7 containing 2-[N-carbamoyl-N-(6-methyl-2-nitrophenyl)-amino]-4-trifluoromethyl-6-ethyl-pyrimidine or 2-[N-carbamoyl-N-(2-nitrophenyl)-amino]-4-trifluoromethyl-6-ethyl-pyrimidine.

9. A method of controlling undesired plant growth which comprises allowing a herbicidally effective amount of a compound according to claim 1 to act on the plant to be controlled or the locus thereof.

10. A method according to claim 9 for the pre- or post-emergence control of undesired plant growth in cereals, cotton, soybeans, rape, maize or rice.

11. A method of influencing plant growth which comprises allowing to act on the plant or the locus thereof an amount of a compound according to claim 1 that is effective in regulating plant growth.

* * * * *